United States Patent [19]
Vincent et al.

[11] 4,086,355
[45] Apr. 25, 1978

[54] NOVEL DISPIRODECANES, PROCESSES FOR THEIR PREPARATION AND PHARMACEUTICAL COMPOSITIONS

[75] Inventors: Michel Vincent, Bagneux; Georges Remond, Versailles; Jean-Claude Poignant, Bures sur Yvette, all of France

[73] Assignee: Science Union et Cie., Societe Francaise de Recherche Medicale, Suresnes, France

[21] Appl. No.: 649,943

[22] Filed: Jan. 19, 1976

[30] Foreign Application Priority Data

Jan. 24, 1975 United Kingdom ............... 3251/75

[51] Int. Cl.$^2$ .................. C07D 487/10; A61K 31/40
[52] U.S. Cl. ............................... 424/274; 260/340.7; 260/340.9 R; 260/338; 260/464; 260/326.5 FM; 260/326.5 D; 260/326.5 CA
[58] Field of Search ............... 424/274; 260/326.5 D

[56] References Cited

U.S. PATENT DOCUMENTS

| 3,238,217 | 3/1966 | Grogan et al. | 260/326.5 D |
| 3,534,054 | 10/1970 | Porter et al. | 260/326.5 D |
| 3,669,986 | 6/1972 | Porter et al. | 260/326.5 D |

OTHER PUBLICATIONS

Jouvet, "Physiological Reviews," vol. 47, #2, pp. 117–142 (1967).
van Twyver, Physiology & Behavior, vol. 4, 901–905.

*Primary Examiner*—Donald G. Daus
*Assistant Examiner*—Mark L. Berch
*Attorney, Agent, or Firm*—Omri M. Behr

[57] ABSTRACT

The invention relates to novel spirodecane derivatives and more specifically to novel azaspirodecane diones.

The invention also provides process for producing said azaspirodecane diones which consists mainly in cyclizing a disubstituted glutaronitrile or a glutaric acid in the presence of an amino compound.

The compounds of the present invention have interesting pharmacological properties and they find therapeutical uses.

10 Claims, No Drawings

NOVEL DISPIRODECANES, PROCESSES FOR THEIR PREPARATION AND PHARMACEUTICAL COMPOSITIONS

PRIOR ART

The prior art may be illustrated by:
U.S. Pat. No. 3,257,398 (to C. H. Grofan and L. M. Rice)
U.S. Pat. No. 3,669,986 (to Hershel D. Porter)

SUMMARY OF THIS INVENTION

This invention relates to novel spirodecane derivatives and to processes for the manufacture thereof.

The present invention provides a compound of the formula I:

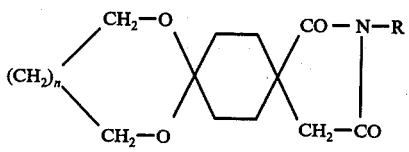

wherein $n$ is an integer of 0 to 3 and R is selected from the group consisting of a hydrogen atom, a lower alkyl radical, an aryl lower alkyl radical, a cyclohexyl radical and a lower alkenyl radical.

The compounds of the invention are endowed with interesting pharmacological properties, namely anti-convulsant and sedative properties. They may find a therapeutic use as a sedative, an anxiolytic drug or a sleep-inducing compound. They may also be helpful in improving the learning and the acquiring of learned memories. They are used in the form of pharmaceutical compositions, namely in unit dosage form suitable for oral, parenteral, sublingual or rectal administration.

This invention also relates to a method for treating epilepsy and insomnia in which a small but effective dose of a compound of general formula is administered in the form of a pharmaceutical composition to a patient suffering from epilepsy.

The processes described in this patent application is directed to the step which consists in cyclising a cyclohexyl succino nitrile or a cyclohexyl succinic acid in the presence of an amino compound and recovering the desired 3-azaspirodecane.

PREFERRED EMBODIMENTS

This invention relates to dispirodecanes, to processes for their preparation and to pharmaceutical compositions containing them.

The present invention provides 3-aza-dispirodecane-2,4-diones of the general formula:

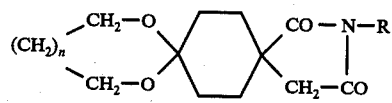

in which $n$ is zero or an integer of from 1 to 3, and

R is a hydrogen atom or a lower alkyl radical, a cyclohexyl radical, an aryl-lower alkyl radical or a lower alkenyl radical.

According to the present invention, $n$ may be 0, in which case there is a direct bond between the two adjacent methylene groups, or $n$ may be 1, 2 or 3, in which case the resulting compounds are derivatives of 1,3-dioxane, 1,3-dioxepane or 1,3-dioxocan.

By the term "lower alkyl radical" there is meant an alkyl radical having from 1 to 6 carbon atoms in a straight or branched chain which may be substituted by, for example, an hydroxyl, a lower alkoxy or a dilower alkyl amino radical. Examples of such lower alkyl radicals are the methyl, ethyl, iso-propyl, sec-butyl, neopentyl, tert-butyl, n-hexyl and diethylaminoethyl radicals.

By the term "lower alkenyl radical" used in this specification there is meant an unsaturated hydrocarbon radical having one or two double bonds and containing from 2 to 6 carbon atoms. Such a radical is preferably a vinyl, allyl, pent-1-enyl, methylallyl, dimethylallyl, butenyl, butadienyl or penta-2,4-dienyl radical.

By the term "aryl-lower alkyl radical" there is meant a phenyl — or substituted phenyl — alkyl radical, the alkyl moiety of which has from 1 to 4 carbon atoms in a straight or branched chain. The phenyl ring may be substituted by, for example, one or more methoxy, trifluoromethyl or chloro radicals. Examples of aryl-lower radicals are the 3,4-dimethoxy-benzyl, benzyl, m-trifluoromethyl-benzyl, α-methyl-benzyl, p-chlorobenzyl, phenylethyl, phenyl-propyl and β-methylphenylethyl radicals.

The compounds of the present invention possess interesting pharmacological properties, especially sedative and anti-convulsive properties. They find therapeutic use as sedative or as sleep-inducing compounds and as drugs which improve the ability to learn and which assist the memory.

In view of their pharmacological properties, the following compounds are especially preferred:

3-methyl-3-aza-9,12-dioxadispiro[4,2-4,2]tetradecane-2,4-dione, 3-aza-9,13-dioxadispiro[4,2-5,2]pentadecane-2,4-dione, and 3-aza-9,12-dioxadispiro[4,2-4,2]tetradecane-2,4-dione.

For therapeutic use, the compounds of the present invention may be formulated as pharmaceutical compositions which comprise, as active ingredient, at least one compound of the general formula I in admixture or conjunction with a pharmaceutically suitable carrier.

Such pharmaceutical compositions are preferably in a form suitable for buccal, parenteral, sublingual or rectal administration. For example, they may be in the form of injectable solutions or suspensions packed in ampouls, phials, multidosage flasks or auto-injectable syringes; tablets, coated tablets, dragees, pills, capsules, drinkable suspensions or solutions or syrups; or sublingual tablets or suppositories.

Their posology may vary over a wide range depending on the age and weight of the patient and on the therapeutic use; it may extend from 50 to 500 mg par unit dosage administered once to four times a day; the preferred dosage ranges from 100 to 300 mg per unit dosage, in the man.

The present invention also provides a process for preparing a compound of the general formula I which comprises submitting a substituted cyclohexanone of the general formula II:

  II in which $R_1$ is a lower alkyl radical, to the action of a lower alkyl cyanoacetate to produce a cyanoalkylidene derivative of the general formula:

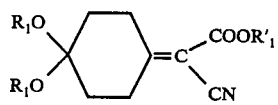  III in which $R_1$ has the meaning given above and $R'_1$ is a lower alkyl radical, condensing the latter with an alkali-metal cyanide in an acidic medium to produce a substituted acetonitrile of the general formula:

  IV in which $R_1$ has the meaning given above, hydrolysing the ketal function thereof to produce a free ketone of the general formula:

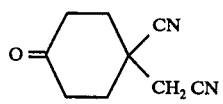  V converting the latter into a cyclic ketal of the general formula:

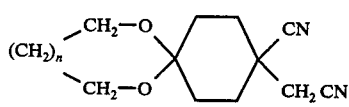  VI in which $n$ is zero or an integer from 1 to 3, by means of a glycol in an acidic medium or by exchange of function with a dioxolane, and cyclising the cyclic ketal in the presence of a lower alkanol and a mineral acid to produce a spirodecane of the formula:

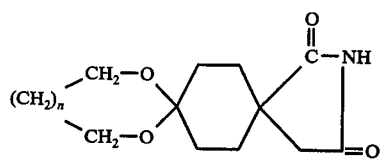  I

The present invention also provides a process for preparing a compound of the general formula I in which a ketal of the general formula VI is hydrolysed to be a substituted acetic acid of the general formula:

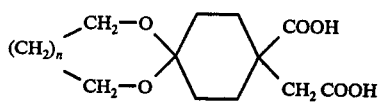  VII in which $n$ has the meaning given above, and the latter is cyclised by heating in the presence of an amino compound of the general formula:

$$RNH_2 \quad \text{VIII}$$

in which R has the meaning given above, to produce a compound of the general formula I:

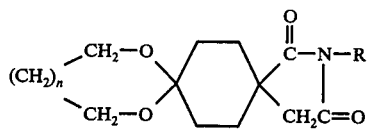  I

The present invention also provides a process for preparing a compound of the general formula I which comprises hydrolysing in an acid medium a substituted acetonitrile of the general formula:

  IV in which $R_1$ has the meaning given above, to produce an aza-spirodecane of the formula:

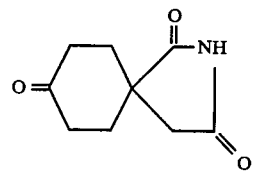  IX and ketalizing the latter by means of a glycol or by functional exchange with a dioxolane to produce a compound of the general formula I.

The present invention also provides the following compounds produced as intermediate products during the processes of the present invention:

the cyano alkylidene derivatives of the general formula III, especially ethyl-4-diethoxycyclohexylidene cyano-acetate;

the compounds of the general formula IV, especially (1-cyano-4,4-diethoxycyclohexyl) acetonitrile;

the compound of the formula:

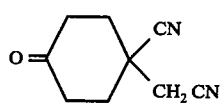  V the cyclic ketals of the general formula IV, especially (1-cyano-4,4-ethylenedioxycyclohexyl) acetonitrile and (1-cyano-4,4-trimethylenedioxycyclohexyl) acetonitrile;

the substituted acetic acids of the general formula VII, especially (1-carboxy-4,4-ethylenedioxycyclohexyl) acetic acid;

the aza spirodecane of the formula:

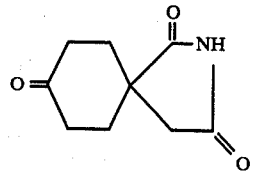

The following examples illustrate the invention. The temperatures are expressed in degrees centigrade.

Preparation of 4,4-diethoxycyclohexanone

STEP A

Ethyl-4,4-diethoxypimelate

Into a three-neck flask, there are successively added 222 g ethyl orthoformate, 230 g ethyl α-oxopimelate and 800 ml ethanol. Hydrogen chloride is then bubbled into the mixture until the pH reaches 1. The mixture is then stirred for 4 days at room temperature and then neutralized by adding a 2 M solution of sodium hydroxide in aqueous ethanol. The precipitate which forms is separated by filtration and the clear filtrate is evaporated to dryness on a steam bath. There are obtained 315.6 g of ethyl 4,4-diethoxy-pimelate, boiling at 129°–133° under 0.05 mm Hg $n_D^{19} = 1.4390$.

STEP B

Ethyl 5,5-diethoxy-2-oxocyclohexane carboxylate 8.4 g finely divided sodium are suspended in 70 ml stirred benzene and 110 ml ethanol are added portionwise in order to produce a slight ebullition.

Ebullition continues until full dissolution of the sodium. Excess ethanol is distilled off while maintaining the amount of solvent constant by adding benzene. The mixture is then left overnight. 76 g of ethyl 4,4-diethoxypimelate are dissolved in 190 ml benzene and added to the benzenic suspension of sodium ethanolate. The whole mixture is then refluxed for 3 hours while maintaining constant the amount of solvent by adding benzene. The reaction mixture is allowed to return to room temperature and then cooled to about 5°. The excess of sodium ethanolate is destroyed by adding about 22 g acetic acid while maintaining the temperature of the reaction mixture below 10°. 200 ml water are then added while cooling in an ice bath. The benzenic phase is separated, the aqueous phase is extracted three times with benzene and the organic phases are united, washed with water, with an aqueous solution of sodium carbonate and again with water, dried over magnesium sulphate and the benzene distilled off. The residue consisting substantially of ethyl 5,5-diethoxy-2-oxocyclohexane carboxylate weighs 60.55 g. It is purified by fractional distillation. The pure product boils at 87°–89° under 0.03 mm Hg (yield 53.9 g) — $n_D^{20} = 1.4728$ UV spectrum (CHCl$_3$) π max 257 mμ $E_{1cm}^{1\%} = 359$

STEP C 4,4-diethoxycyclohexanone

Into a flask are successively added 38.7 g of ethyl 5,5-diethoxy-2-oxocyclohexane carboxylate and 215 ml of a 10% potassium hydroxide solution. The mixture is refluxed for 16 hours, then cooled to room temperature. The organic phase is extracted twice with ether; the aqueous solution is salted out with potassium carbonate and an oily phase separates which is extracted with ether. The ethereal phases are united, dried over potassium carbonate and evaporated to dryness. The crude residue weighing 26.4 g is purified by distillation under reduced pressure. The yield amounts to 22.3 g of a liquid boiling at 110°–112° under 12 mm Hg — $n_D^{22} = 1.449$.

EXAMPLE I

3-Aza-9,13-dioxadispiro[4,2-5,2]pentadecane-2,4-dione

Step A 1-(cyano-4,4-diethoxycyclohexyl)acetonitrile 55.8 g 4,4-diethoxycyclohexanone are dissolved in a mixture of 50 ml benzene, 31.6 g ethyl cyano-acetate, 0.75 g acetic acid and 0.75 g piperidine. The reaction mixture becomes yellow and is refluxed for 3 hours. The water formed during the reaction is extracted as an azeotropic mixture. Once the theoretical amount of water is thus obtained the mixture is allowed to cool to room temperature.

19.2 g potassium cyanide dissolved in 42 ml water are added dropwise over 1 hour while stirring and keeping the mixture at 40°. The mixture is then left in a cool place overnight, and neutralized by adding 0.94 g potassium carbonate in 3.7 ml water. The whole mixture is refluxed for 6 hours, then left to stand. The aqueous phase is discarded. The benzenic phase is washed with water, dried over sodium sulphate, filtered and concentrated under vacuum. The brownish oily residue is taken up in hot pentane and the solution is left overnight. Crystallization is initiated by scratching: the crystalls obtained are separated by filtration, dried, washed with pentane and dried again. 56.2 g of (1-cyano-4,4-diethoxycyclohexyl)acetonitrile, melting at 74°–75°, are obtained.

Step B (1-cyano-4-oxocyclohexyl)acetonitrile

In a flask 14.1 g of (1-cyano-4,4-diethoxycyclohexyl)acetonitrile are suspended in 100 ml 4N hydrochloric acid and stirred for 1 hour on a boiling water bath. The mixture is then cooled and the resulting crystallised mass is sucction-filtered, dried, washed with water and dried at 60° in an oven.

7.9 g of (1-cyano-4-oxocyclohexyl)acetonitrile are thus obtained, melting at 154°–155°.

Step C (1-cyano-4,4-trimethylenedioxycyclohexyl)acetonitrile 15 g of (1-cyano-4-oxocyclohexyl)acetonitrile obtained according to Step B are mixed with 9.43 g propane 1,3-diol, 200 ml toluene and few mg of p-toluenesulphonic acid. The whole mixture is refluxed for 3 hours. The water formed (about 2 ml) is discarded and the toluene solution is washed several times with a 10% aqueous solution of sodium bicarbonate, then with water until neutral, dried over sodium sulphate, filtered and concentrated under reduced pressure.

16.9 g of (1-cyano-4,4-trimethylenedioxycyclohexyl)acetonitrile are obtained, melting at 124°–125°.

The product is further purified by recrystallization from ethanol. The melting point is increased to 125° C.

| Analysis | $C_{12}H_{16}O_2 = 220.27$ | | |
|---|---|---|---|
| | C | H | N |
| Calculated | 65.43 | 7.32 | 12.71 |

-continued

| Analysis | $C_{12}H_{16}O_2 = 220.27$ | | |
|---|---|---|---|
| | C | H | N |
| Found | 65.47 | 7.31 | 12.76 |

Step D

3-Aza-9,13-dioxadispiro[4,2-5,2]pentadecane-2,4-dione

To 50 ml of a saturated solution of hydrochloric acid in methanol at 10° there are added 16.9 g of (1-cyano-4,4-trimethylenedioxycyclohexyl)acetonitrile. The yellow solution formed is kept in cool place for two days. It is then refluxed for 4 hours and allowed to cool to room temperature. The insoluble matter is separated, washed with few milliliters of methanol and dried. The washings and the filtrate are united and concentrated under reduced pressure until semi-crystalline. The mixture is taken up in 15 ml hot isopropanol on a water bath until complete dissolution is obtained. The mixture is then left to stand at room temperature. The crystals which appear are separated, washed with cold isopropanol and dried in vacuo. 7.5 g of 3-aza-9,13-dioxadispiro[4,2-5,2]pentadecane-2,4-dione are recovered. They are purified by dissolving in 50 ml acetonitrile, filtering off the insoluble matter, concentrating to half volume and adding to the concentrated solution 25 ml water. The mixture becomes cloudy and a crystalline precipitate separates. The mixture is stirred for one hour on an ice bath and then filtered; the precipitate is washed with water then dried.

3.6 g of pure product are obtained melting at 190°.

| Analysis | $C_{12}H_{17}O_4N = 239.27$ | | |
|---|---|---|---|
| | C | H | N % |
| Calculated | 60.23 | 7.16 | 5.85 |
| Found | 59.88 | 7.23 | 5.84 |

EXAMPLE II 3-aza-9,12-dioxadispiro[4,2-4,2]tetradecane-2,4-dione

Step A

3-Azaspiro[4,5]decane-2,4,8-trione

To 75 ml of a saturated methanolic solution of hydrochloric acid there are added at about 10° 18.2 g of (1-cyano-4-oxocyclohexyl)acetonitrile. The mixture is allowed to stand for two days, refluxed for 4 hours, and then filtered. The filtrate is concentrated and the crystals which appear are separated, washed with methanol and dried. 7 g of 3-azasprio[4,5]decane-2,4,8-trione are recovered, melting at 154°.

Recrystallisation from acetonitrile does not increase the melting point.

Step B 6.5 g of 3-azaspiro[4,5]decane-2,4,8-trione are dissolved in 6.2 ml of tetrahydrofuran and 5.3 ml ethyleneglycol. To this solution 5.3 ml of boron trifluoride etherate are added and the reaction mixture is stirred overnight. After standing for a few hours, the mixture is filtered and the filtrate is neutralized by adding a saturated solution of sodium bicarbonate. The aqueous phase is decanted and extracted with ether. The ethereal solution is united with the organic phase and concentrated on a steam bath, giving 7.8 g yellow crystals of crude 3-Aza-9,12-dioxadispiro[4,2-4,2]tetradecane-2,4-dione. The crude product is dissolved in 20 ml warm ethanol. Upon cooling, crystalls separate, are filtered, washed with ethanol then pentane and dried. 3.5 g of pure compound are obtained, melting at 154°-155°.

A mixture of this compound and the compound of step A has a depressed melting point of about 130°.

Recrystallization from ethanol raises the melting point to 157°-158°.

EXAMPLE III

3-Aza-9,12-dioxadispiro[4,2-4,2]tetradecane-2,4-dione(1-cyano-4,4-ethylenedioxycyclohexyl)acetonitrile 5 g of (1-cyano-4-oxocyclohexyl)acetonitrile are added to 2.3 ml ethyleneglycol, 200 ml toluene and few mg of p-toluenesulphonic acid. The mixture is refluxed for about 6 hours. After the usual treatment of the toluene phase, 5.6 g of (1-cyano-4,4-ethylenedioxycyclohexyl)acetonitrile are recovered, melting at 112°-113°. The melting point is unchanged after recrystallisation from ethanol.

| Analysis | $C_{11}H_{14}O_2N_2 = 206.24$ | | |
|---|---|---|---|
| | C | H | N % |
| Calculated | 64.06 | 6.84 | 13.58 |
| Found | 63.66 | 6.78 | 13.36 |

Infra-red spectrum

Stretchings at 2250 and 2260 cm$^{-1}$(cyano) — absence of a carbonyl band.

Step B 5.6 g of (1-cyano-4,4-ethylenedioxycyclohexyl)acetonitrile are suspended in 50 ml of a saturated methanolic solution of hydrochloric acid at $-5°$ C in a cooling mixture. When dissolution is complete, cooling is stopped and the temperature allowed to rise to 10°. After 48 hours standing, the yellow solution is refluxed for 4 hours and then filtered when cold, in order to separate insoluble matter. The filtrate is placed in a cool place and crystallization soon begins. The crystals — consisting essentially of mineral salts — are filtered and the clear filtrate is concentrated under vacuum to very small volume. The crystals which then form are separated by filtration, dried, washed with ethanol and then with pentane and dried at 40°. 2.5 g of 3-Aza-9,12-dioxadispiro[4,2-4,2]tetradecane-2,4-dione are obtained which after recrystallization from acetonitrile is in the form of white crystals melting at 157°.

A mixture of this compound and that obtained from the ketalization step of Example II does not exhibit any depression of the melting point.

| Analysis | $C_{11}H_{15}O_4N = 225.25$ | | |
|---|---|---|---|
| | C | H | N % |
| Calculated | 58.65 | 6.71 | 6.21 |
| Found | 58.59 | 6.62 | 6.14 |

EXAMPLE IV

3-methyl-3-aza-9,12-dioxadispiro[4,2-4,2]tetradecane-2,4-dione

Step A (1-carboxy-4,4-ethylenedioxycyclohexyl)acetic acid 20.6 g of (1-cyano-4,4-ethylenedioxycyclohexyl)acetonitrile obtained according to step A of Example III are suspended in 160 ml of a 20% aqueous solution of potassium hydroxide and refluxed for 8½ hours. The mixture is then cooled and an oily product separates. The mixture is filtered and the filtrate is extracted twice with ether. The aqueous solution is then rendered acidic by adding concentrated hydrochloric acid until the pH reaches 3.5, then 4 N hydrochloric acid to pH 3. (1-Cyano-4,4-ethylenedioxycyclohexyl)acetic acid which remains in the aqueous solution is extracted for one day with ether in a liquid-liquid extractor. The ethereal phase is separated, dried over sodium sulphate, filtered and concentrated. There remains an oily residue which crystallizes quickly. The crystals are filtered and dried, giving a residue weighing 15.9 g and melting at 137°.

Recrystallisation furnishes white crystals melting at 142°–143°.

Under similar conditions, (1-cyano-4,4-trimethylenedioxycyclohexyl)acetonitrile is hydrolised to (1-carboxy-4,4-trimethylenedioxycyclohexyl)acetic acid.

Step B 3-methyl-3-aza-9,12-dioxadispiro[4,2-4,2]tetradecane-2,4-dione

In a small flask there are successively added 15.9 g of (1-carboxy-4,4-ethylenedioxycyclohexyl)acetic acid and 12.2 g of a 33% aqueous solution of methyl-amine. The mixture is heated on a boiling water bath until a viscous solution is obtained; heated on a metallic bath for 30 minutes until the water is completely distilled off; for a further 10 minutes at about 220° and finally for 30 minutes at about 220°, giving a reddish oil. The residue is then distilled under reduced pressure and a nitrogen atmosphere. It distills at about 167° under 0.15 mm Hg. The crystals obtained are separated and thoroughly dried. 12.7 g of 3-methyl-3-aza-9,12-dioxadispiro[4,2-4,2]tetradecane-2,4-dione are recovered.

The crude product is taken up in 30 ml hot ethanol. Upon cooling, crystallisation begins. The precipitate is suction-filtered, washed with cold ethanol and ether and dried at 50°. 9.9 g of pure product are obtained melting at 141°–142°. The yield amounts to 63.8%.

Infra red spectrum: carbonyl at 1.760 and 1.690 cm$^{-1}$.

In a similar manner but starting from cyclohexylamine instead of methylamine, 3-cyclohexyl-3-aza-9,12-dioxadispiro[4,2-4,2]tetradecane-2,4-dione is obtained; starting from propylamine, 3-propyl-3-aza-9,12-dioxadispiro[4,2-4,2]tetradecane-2,4-dione is obtained; starting from β-phenylethylamine, 3-phenylethyl-3-aza-9,12-dioxadispiro[4,2-4,2]tetradecane-2,4-dione is obtained; starting from tert.butylamine, 3-tert.butyl-3-aza-9,12-dioxadispiro[4,2-4,2]tetradecane-2,4-dione is obtained; starting from 2-methoxy-1-aminoethane, 3-(2-methoxyethyl)-3-aza-9,12-dioxadispiro[4,2-4,2]tetradecane-2,4-dione is obtained; starting from pent-1-enyl-5-amine, 3-(pent-1-enyl)-3-aza-9,12-dioxadispiro[4,2-4,2]tetradecane-2,4-dione is obtained. Similarly, using (1-carboxy-4,4-trimethylenedioxycyclohexyl)acetic acid and homo-veratrylamine, 3-(3,4-dimethoxybenzyl)-3-aza-9,13-dioxadispiro[4,2-5,2]pentadecane-2,4-dione is obtained.

Pharmacological Study of the Compounds of the Invention

Acute Toxicity

The average lethal dose has been determined on batches of mice (strain CD) weighing from 18 to 22 grams each, which received increasing doses of the tested compounds intraperitoneally. The average lethal dose by this mode of administration has been calculated graphically and ranges from 1 g to 1.5 g/kg bodyweight.

Effect on the Central Nervous System

The first dosage level, administered either orally or intraperitoneally which produced a physiologically observable effect induced an ebrious walk. At higher dosage levels (350 mg/kg) the motility of the test animals at first increases and then decreases following which the test animals sleep. At all the dosage levels of 1 g/kg bodyweight, no neurological symptoms, other than sleep, appear.

Anti-Convulsant Effect (a) pentamethylene tetrazole test

The anti-convulsant effect of the compounds of the invention has been tested on the pentamethylene tetrazole convulsion inducing test. The tested compounds were administered orally or intraperitoneally thirty minutes before intravenous administration of 100 mg/kg pentamethylene tetrazole. Administration of pentamethylene tetrazole has the effect of eliciting tonic and clonic spasms and finally death. The delay in appearance of the spasms, the duration of the spasms and the mortality for each batch of test animals was determined.

The average dosage which increases by 100% the latency — i.e., the delay in appearance of the spasms — was approximately 100 mg/kg by intraperitoneal administration and approximately 150 mg/kg by oral administration.

Under similar conditions, Ethosuximide selected as a comparison substance required a dosage level of 200 mg/kg by oral administration.

(b) Electro-shock test

Batches of mice were subjected to the effect of an electric shock caused by a 60 hz/100 v current for 110 milliseconds. One hour before the test, the mice received orally or intraperitoneally the compounds to be tested at doses ranging from 100 to 500 mg/kg.

The average dosage which inhibits totally — i.e., 100% — the tonic convulsions has been found to be about 200 mg/kg (intraperitoneal administration) and about 400 mg/kg (oral administration). Under similar conditions, Ethosuximide even at a dosage of 1,000 mg/kg (oral administration) does not totally inhibit the occurrence of tonic convulsions.

Effect on the Electro Encephalogram in Rats

The tested compounds have been administered intraperitoneally in aqueous solution to batches of male rats (CD strain). At 75 mg/kg the traces are normal and the alternations of arousal and sleep were normal.

At 100 mg/kg the rats have a depressed look. The motility is decreased. The type of sleep which normally appears only after 60 minutes is often present after 5 to 10 minutes subsequent to treatment. Occasionally, the advent of paradoxical sleep for short periods is noted. The arousal reactions are quite normal.

At a dosage of 200 mg/kg at which level the electro shock induced convulsions are totally inhibited, a large increase of slow sleep is noted. The arrest reactions are of short duration (10 seconds). In one animal out of two, significant proportions of paradoxical sleep are noted. During the few arousal periods, the traces are normal, rapid, and of small amplitude.

It is to be concluded from the EEG results that even high dosage levels of administration of the compounds of the invention do not appear to give rise to pathological effects. A state of sedation is induced at high dosages (100 mg/kg and more) combined with a look of depression in the test subject and a decrease in their motility. In spite of this depression of central origin, the arousal periods may be explained as an underlying state of excitation. This remaining excitability may have caused the increases of the paradoxical sleep.

What we claim is:

1. 3-aza-dispirodecane-2,4-diones of the formula I:

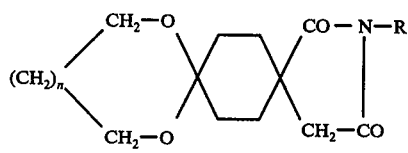

in which $n$ is zero or an integer of from 1 to 3,

R is hydrogen, a lower alkyl having from 1 to 6 carbon atoms, a monosubstituted lower alkyl radical wherein the substituent is a member selected from the group consisting of hydroxy, lower alkoxy and dilower alkyl amino; a cyclohexyl; an aryl lower alkyl wherein the aryl radical is a member selected from the group consisting of phenyl, methoxyphenyl, trifluoromethylphenyl and chlorophenyl, and lower alkenyl having 2 to 6 carbon atoms.

2. The compounds of claim 1 in which $n$ is defined as above, and R is hydrogen or lower alkyl, a substituted lower alkyl, cyclohexyl or aryl lower alkyl.

3. 3-methyl-3-aza-9,12-dioxadispiro[4,2-4,2]tetradecane-2,4-dione, according to claim 1.

4. 3-aza-9,13-dioxadispiro[4,2-5,2]pentadecane-2,4-dione, according to claim 1.

5. 3-aza-9,12-dioxadispiro[4,2-4,2]tetradecane-2,4-dione, according to claim 1.

6. The compositions having hypnotic and/or antiepileptic activity which comprise, as active ingredient, at least one compound of claim 1 in admixture or conjunction with a pharmaceutically suitable carrier.

7. A composition according to claim 6 in a form suitable for buccal, parenteral, sublingual or rectal administration.

8. A composition according to claim 6 wherein the amount of active ingredient ranges from 50 to 500 mg per unit dosage.

9. A method for treating insomnia or epilepsy in warm-blooded animals which comprises administering to warm-blooded animals suffering from said ailments a safe but effective amount of a compound of claim 1.

10. The method of claim 9 wherein the safe but effective amount of active compound ranges from 50 to 2000 mg per day.

* * * * *